(12) United States Patent
Somers et al.

(10) Patent No.: US 6,587,036 B2
(45) Date of Patent: Jul. 1, 2003

(54) MULTIPLE MEDICATION REMINDER

(76) Inventors: Scott R. Somers, 77 Symons St., Richland, WA (US) 99352; Gregory M. Somers, 5900 N. Starr Rd., Newman Lake, WA (US) 99025; Ronald G. Stokes, 204 S. Century Ct., Veradale, WA (US) 99037

( * ) Notice: Subject to any disclaimer, the term of this patent is extended or adjusted under 35 U.S.C. 154(b) by 0 days.

(21) Appl. No.: 09/916,626

(22) Filed: Jul. 26, 2001

(65) Prior Publication Data

US 2003/0020599 A1 Jan. 30, 2003

(51) Int. Cl.[7] .............................................. G08B 1/00
(52) U.S. Cl. ........................... 340/309.16; 340/309.4; 340/309.7
(58) Field of Search ........................ 340/309.16, 309.3, 340/309.4, 309.5, 309.7, 309.8; 368/10, 12, 21, 109, 261

(56) References Cited

U.S. PATENT DOCUMENTS

| | | | |
|---|---|---|---|
| 4,258,354 A | * 3/1981 | Carmon et al. | 340/309.4 |
| 4,490,711 A | 12/1984 | Johnston | 340/309.4 |
| 4,725,999 A | 2/1988 | Tate | 368/10 |
| 4,962,491 A | 10/1990 | Schaeffer | 368/21 |
| 5,097,429 A | 3/1992 | Wood et al. | 702/177 |
| 5,157,640 A | 10/1992 | Backner | 368/10 |
| 5,159,581 A | * 10/1992 | Agans | 368/10 |
| 5,724,021 A | 3/1998 | Perrone | 340/309.15 |
| 5,805,051 A | 9/1998 | Herrmann et al. | 340/309.4 |
| 5,861,797 A | 1/1999 | Becker | 340/309.3 |
| 6,018,289 A | 1/2000 | Sekura et al. | 340/309.4 |
| 6,104,674 A | * 8/2000 | Emoff et al. | 368/109 |
| 6,225,920 B1 | * 5/2001 | Dayle | 341/21 |

* cited by examiner

*Primary Examiner*—Van Trieu
(74) *Attorney, Agent, or Firm*—Reidlaw, L.L.C.; John S. Reid

(57) ABSTRACT

Apparatus for reminding a person to perform a plurality of periodically repeating tasks includes a first and a second user-accessible interface each having at one least task switch. A first and a second signal device each correspond to the respective first and second user-accessible interfaces. A surface supported by the apparatus can be imprinted with first and second task identifications which are aligned proximate to the corresponding signal devices and user interfaces. The apparatus includes an electronic processor configured to set a first alarm interval and a second alarm interval in response to the at least one task switch of the respective first or second user-accessible interface being accessed by a user a single time. The processor measures the passage of time using an electronic timing device and activates the first or second signal device when the measured passage of time exceeds the respective first or second alarm interval.

21 Claims, 6 Drawing Sheets

MULTIPLE MEDICATION REMINDER

FIELD OF THE INVENTION

The invention claimed and disclosed herein pertains to reminders, in the form of electronic timers and alarms, for notifying a person or persons to perform an action, and in particular to a reminder apparatus for reminding an individual to take or dispense medication.

BACKGROUND OF THE INVENTION

Situations often exist wherein an individual desires to be reminded of certain actions or tasks which need to be performed throughout the day or the week. The more tasks there are to be performed, the more desirable it is to have an automated reminder system capable of reminding the individual of each task as it becomes due. A common situation where reminders of multiple tasks is desirable is an individual who is taking two or more medications having different dosage frequencies, such that the dosage periods do not always coincide. Another similar situation exists wherein a parent is administering different medications to different children, and desires to be reminded of which medication to give to which child at a particular time. The same situation exits for caretakers, such as staff in a nursing home or a day-care, wherein the staff needs to be reminded to administer medications to different patients at different intervals.

As is evident, an apparatus having the capability to remind an individual of various tasks to be performed at different times can be of great use. In the medication dosage area, such an apparatus can help to ensure that medication is taken at the correct times, or administered to the correct individual at the correct times, having a significant effect on the therapeutic value of the medication. In fact, the need for a simple to-use medication reminder device is particularly keen in the situation where a caretaker is required to administer a large number of different medications to a significant number of patients, as in the nursing home setting. Further, with the general shortage of skilled workers available to fill positions in nursing homes and the like, it is not always possible to recruit workers who have complex technical skills allowing them to program complex reminder devices. Thus, it is desirable to provide these workers with an intuitive apparatus which allows then to easily set reminder timers for dispensing a variety of different medications to patients under their care.

A number of different solutions to the problem are provided by the prior art. However, as will be seen, none of the prior art devices offer a simple, essentially pre-programmed solution to the problem. For example:

U.S. Pat. No. 5,861,797 to Becker discloses a reminder timer with the capability to display various "pay attention" notices, and the ability to select the frequency of the notices (i.e., the number of times per day the notice is given). However, this latter feature requires using "up/down" keys to step through various options. While this does offer a simple user interface in that the number of keys or buttons is reduced over other designs, the use of the interface is not inherently intuitive, and thus not as "simple" to use as it may first appear. This is a common trait to many of the prior art devices—that is, in order to "simplify" the user interface, the prior art devices generally provide for a minimal number of buttons (typically a "select function" button and two buttons for scrolling up or down through a series of options) and a digital display, such as an LCD display.

U.S. Pat. No. 5,805,051 to Herrmann describes a multi-medication reminder timer having the ability to select frequencies of dosage for each of a plurality of medications. However, this device is similar to the Becker device in that it employs a user interface which requires entering numerous keystrokes in order for the user/care-giver to program the different alarm sequences.

U.S. Pat. No. 5,157,640 to Backner discloses a multiple-medication reminder timer which provides an alarm and displays the name of the medication to be taken via a programmable display (such as an LCD display). The device is configured to be programmed by a pharmacist via a separate programming unit, and is therefore essentially incapable of being programmed directly by the user, limiting the practicality of the device.

U.S. Pat. No. 4,725,999 to Tate describes a multi-medication reminder/dispenser. The device has a plurality of compartments for holding a plurality of different medications. Each compartment is provided with its own dedicated timer. This simplifies the programming of the various timers by the user. However, each timer is set by turning a dial to correspond to the number of hours between dosages. This requires a user to perform a calculation of the hourly interval, and also to remember or look up the medication frequency for each medication dial. Thus, the user may be confused by the interface and enter the wrong number (that is, the user might accidentally enter "4" instead of "6" when a particular medication is to be taken four times a day).

U.S. Pat. No. 5,097,429 to Wood discloses a multi-medication reminder timer which is not unlike the devices described by Becker and Herrmann. That is, it provides a highly simplified user interface (three buttons and an LDC-type display), yet requires a large number of keystrokes to program the various timer functions, menus and programming options.

U.S. Pat. No. 6,018,289 to Sekura is similar to the Wood device in that it provides a multi-medication reminder timer having a user input interface with few buttons, yet the device allows for a complex regimen of dosages to be entered, and thus requires a long and complex set of data to be entered by the user. The programming of this device is not inherently intuitive.

U.S. Pat. No. 5,724,021 to Perrone describes a single medication reminder timer which is programmable by pressing a single button corresponding to the frequency of dosage of the medication. However, the timer is used in conjunction with only a single medication, and is therefore not practical for reminding a user when multiple medications are involved.

U.S. Pat. No. 4,962,491 to Schaeffer provides for a multi-medication reminder timer which uses a relatively complex user interface to enter the reminder program. This device should be compared to the devices described above which have a simple interface, yet still require a significant number of steps to program. In either case the user interface is not intuitive.

U.S. Pat. No. 4,490,711 to Johnston describes various timer/reminder devices which can be programmed to generate reminder alarms. One such device is a multi-medication dispenser which incorporates a timer/reminder circuit. Johnston describes how the medication reminder provides "ease of programming". However, the programming is accomplished using a punch card to select the dosage intervals. Further, the use of a punch card requires that a new card be generated if a mistake is made while programming. Johnson also provides an alternate method of programming one of the timers using slide switches.

What is needed then is an apparatus for reminding a user of a plurality of tasks to be performed, and wherein the apparatus is simple to operate and which incorporates a user interface which is inherently intuitive. Preferably, the alarms for the various tasks or events to be tracked (e.g., dispensing of medication) can be set using a single keystroke. It is further desirable that the apparatus should be highly portable, and should provide alarms which are inherently comprehensible.

SUMMARY OF THE INVENTION

The invention provides for an apparatus to remind a person to perform a plurality of periodically repeating tasks. The apparatus is particularly useful to remind a person to take one or more medications, or to administer one or more medications to others. The arrangement of buttons and/or switches used to set the alarms and respond to the alarms is inherently intuitive, making the apparatus particularly easy to use.

In a first embodiment of the invention the reminder apparatus includes a body member, and a first and a second user-accessible interface. Each user interface can be used to set a respective first and second alarm. The user interfaces can include one or more of a push-button, a switch, or a key (such as a capacitance key). Each of the user interfaces has at one least task switch supported by the body member. The task switch (or switches) is/are used to set the alarms. The apparatus includes a first signal device and a second signal device, the signal devices being supported by the body member. The first and second signal devices correspond to the respective first and second user-accessible interfaces, and thus to the respective first and second alarms. A surface is supported by the body member and is configured to be imprinted with a first and a second task identification (such as the names of medications), such that when the task identifications are imprinted on the surface the first and second task identifications are aligned proximate to the corresponding first and second signal devices and the first and second user-accessible interfaces. The apparatus has an electronic processor and an electronic timer in communication with the processor. The processor is in electronic communication with the first and second user-accessible interfaces and the first and second signal devices. Preferably, the processor is configured to set a first alarm interval in response to the at least one task switch of the first user-accessible interface being accessed by a user a single time. The processor is further preferably configured to set a second alarm interval in response to the at least one task switch of the second user-accessible interface being accessed by a user a single time. The processor measures the passage of time using the electronic timing device, and activates the first signal device when the measured passage of time exceeds the first alarm interval. The processor activates the second signal device when the measured passage of time exceeds the second alarm interval.

In a first version of the first embodiment, the user interface includes a single task switch for each separate task. The signal device for each task consists of a plurality of light emitting diodes (LEDs). Each diode can correspond to a daily interval frequency (e.g., once a day, twice a day, three times a day, and so on). By pressing and holding the task switch, the LEDs are individually illuminated in series. When the LED corresponding to the daily alarm frequency desired is illuminated, the task switch is released, thus programming the apparatus to periodically alarm at the established frequency.

In a second variation of the first embodiment of the present invention, the user interface includes a plurality (or series) of task switches for each task. Each task switch in each series corresponds to a daily interval frequency (e.g., once a day, twice a day, three times a day, and so on). By pressing a task switch corresponding to the daily alarm frequency desired, the apparatus is thus programmed to periodically alarm (for that task) at the established frequency. This provides for an intuitive interface allowing a user to easily set the alarms. The signal device can be a single LED for each task. The signal device can also include an audible signal, which can be varied depending on the task for which an alarm signal is being generated. For example, a single tone, repeating every ten seconds, for the first task, and two tones, repeating every ten seconds, for the second task.

These and other aspects and embodiments of the present invention will now be described in detail with reference to the accompanying drawings, wherein:

DETAILED DESCRIPTION OF THE INVENTION

The present invention provides an apparatus for reminding an individual of a plurality of tasks to be performed. The apparatus is particularly useful in reminding an individual to take a variety of medications at different times during the day, or reminding a care-giver to administer a variety of medications to different individuals at different times throughout the day. Generally, the apparatus provides for a plurality of reminders or alarms to be set, each corresponding to a different task to be performed, such as taking a particular medication. Specifically, the alarm for any particular task can be set (i.e., "programmed") by using a single key or button without the requirement for complex menu systems. More specifically, the alarm for any particular task can be set by using a single stroke of a key or button associated with the particular task.

Figure 1:
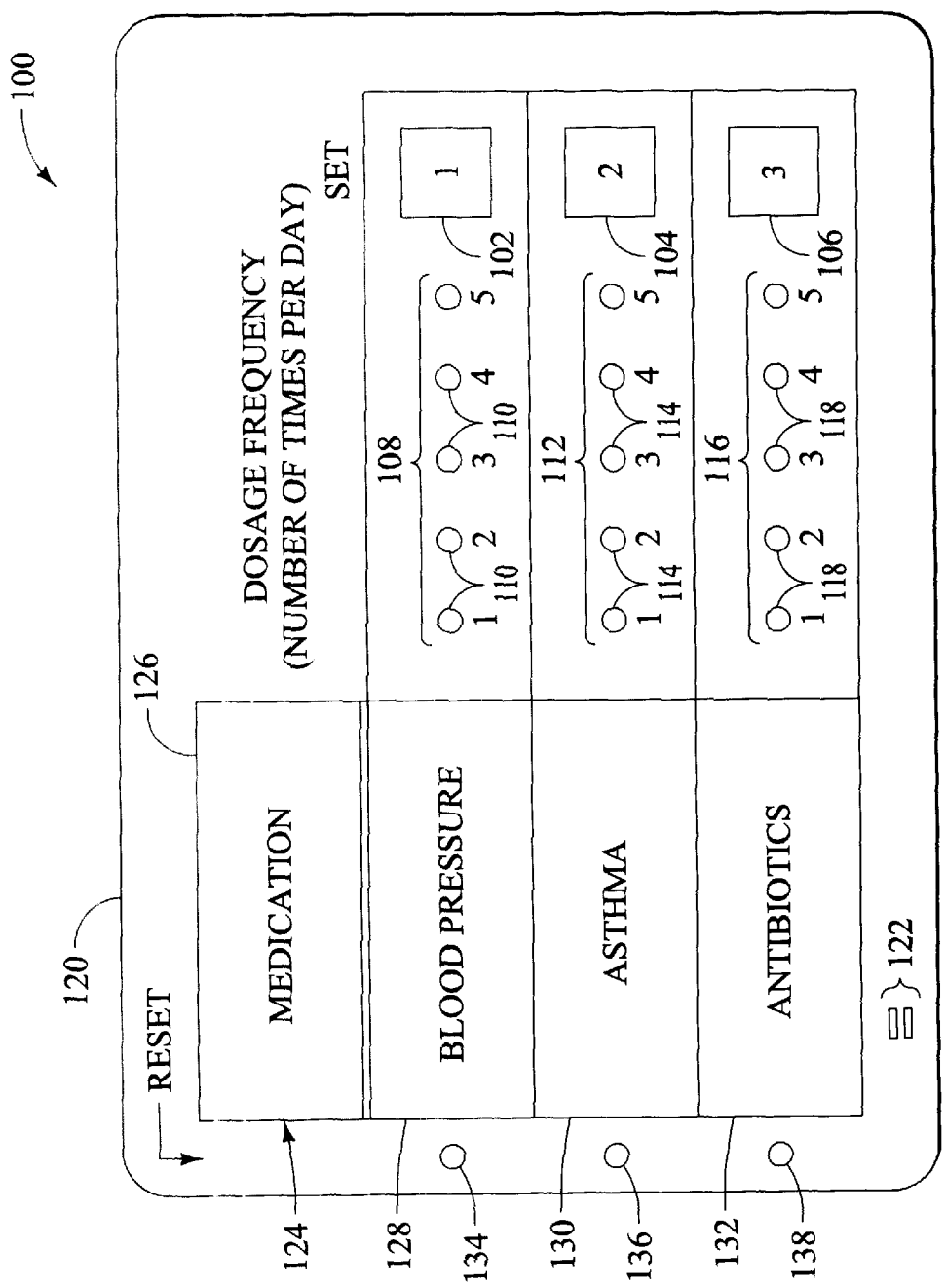
FIG. 1 is a plan view of an apparatus in accordance with a first embodiment of the present invention.

Turning now to FIG. 1, a plan view of an apparatus 100 in accordance with a first embodiment of the present invention is depicted. The reminder apparatus 100 is depicted as being a certain size, although current technology allows the apparatus 100 to be manufactured having a plan view surface area approximately equal to that of a standard credit card, i.e., 8.6 cm by 5.5 cm. Further, current technology allows the apparatus to be manufactured to a thickness of about 3 mm. In this way the apparatus can be carried by the user in a wallet or a purse in the same manner that a credit card is carried. It should be understood that the apparatus 100 can be any size, and that in some instances (e.g., for use by visually impaired persons) it can be desirable to manufacture the device to a larger size so that it can more easily be seen and operated by such persons.

The apparatus 100 depicted in FIG. 1 is configured to provide reminders for an individual for up to three tasks.

However, the reminder device can also be configured to provide reminders for more or less tasks. In this manner, consumers can be offered a variety of devices providing for different numbers of task reminders. When a large number of task reminders are provided (for example, more than 5), it may be convenient to increase the size of the apparatus beyond the "credit-card" size. Further, additional reminders typically increase the cost of manufacturing the apparatus, and so a consumer may desire to purchase a reminder apparatus which allows for a smaller number of task reminders than can be provided for by the present invention. Thus, offering a range of reminder apparatuses having differing numbers of task reminders will allow consumers to obtain a reminder device best suited to their needs and budgets.

The reminder apparatus 100 of FIG. 1 has a body member 120. The body member can include a face plate, a rear plate, and a circuit board sandwiched between the face plate and the rear plate. However, the body 120 is not limited to this configuration. For example, the body 120 can comprise only a face plate and a rear plate, and circuit components can be inserted into recesses formed within one or both of the plates. Further, the body member can comprise a single element with circuit members housed therein.

The apparatus 100 further comprises a plurality of user-accessible interfaces. There is a separate user interface for each task reminder. In the apparatus 100, the user interfaces each comprise a single user-accessible task switch. For the first reminder, the user interface comprises first task switch 102; for the second reminder, the user interface comprises second task switch 104; and for the third reminder, the user interface comprises third task switch 106. The operation of the task switches will be described further below.

The apparatus 100 also includes a separate signal device for each task reminder. For the first reminder, the signal device 108 comprises first plurality of light emitting diodes ("LEDs") 110; for the second reminder, the signal device 112 comprises a second plurality of LEDs 114; and for the third reminder, the signal device 116 comprises a third plurality of LEDs 118. The operation of the signal devices will be described further below.

The body 120 of the apparatus 100 supports a surface 124 which can be imprinted with the various task identifications for which reminders are to be provided. The surface 124 can be a designated area on the face of the body 120, or the body 120 can be configured to receive an essentially planar component, such as a card, which can be removed from the apparatus. When the surface 124 is part of the body 120, it can be a writeable-erasable surface, such as enameled metal or plastic. The surface can then be imprinted with an erasable ink to identify tasks to be performed, and can thus be erased and later reimprinted with different tasks. When the surface 124 is removable from the body it can be configured to be imprinted a single time, such as a piece of laminated cardboard or paper, or it can be a writeable-erasable surface, such as a plastic surface. In FIG. 1, the apparatus 100 is configured to remind a user to take or administer medications at prescribed intervals. Thus, the surface 124 can be provided with a permanent identifier 126 (here, "Medications") of the type of tasks to be listed below the header 126. For example, as depicted in FIG. 1, the first "task" identification is 128, "BLOOD PRESSURE" for medication to control blood pressure, the second "task" identification 130 is "ASTHMA" for medication to control asthma, and the third "task" identifier 132 is "ANTIBIOTICS" for antibiotics to be taken by an individual.

Preferably, the task identifications 128, 130 and 132 are aligned proximate the respective signal devices 108, 112 and 116, as well as proximate the respective task switches 102, 104 and 106. In this way the task identifiers, the signal devices, and the task switch for the same task are all aligned in the same row, providing relatively immediate visual comprehension of the apparatus to a user. That is, for example, a user will inherently understand that the signal devices 112 and the task switch 104 are associated with the task 130. This eliminates the need for complex menu systems, and also reduces confusion by the user when using the apparatus. Although in the example depicted in FIG. 1 the task switches, signal devices and task identifiers are shown as being in a horizontal row, they can also be arranged in a vertical row (i.e., a "column") to equal effect.

The reminder apparatus 100 can also include a separate reset switch for each task reminder, although, as will be explained below, the function performed by the reset switches can also be performed by the task switches 102, 104 and 106. In the example depicted in FIG. 1, the apparatus 100 includes a first reset switch 134 for the first task reminder, a second reset switch 136 for the second reminder, and a third reset switch 138 for the third reminder.

In addition to the signal devices 108, 112 and 116, the apparatus 100 can also include an audible alarm or signal 122. The audible alarm can supplement the signal device, as will be explained further below.

The apparatus 100, in the example shown, is configured as a medication reminder device. The device is configured to remind a user to take or administer a plurality of medications on a basis of at least daily. It is understood that the reminder device 100 can also be configured to provide reminders at frequencies of greater than daily. However, in the scenario application medications are required to be taken at least once a day, and so the first LED in each signal device (i.e., the LED numbered "1"), corresponds to a frequency of one time a day. The particular device shown has thus been configured to provide reminders at intervals of every 24 hours or less. Accordingly, for the apparatus 100, the first LED in each signal device (i.e., the LEDs numbered "1"), corresponds to a frequency of one time a day; the second LED in each signal device (i.e., the LEDs numbered "2"), corresponds to a frequency of twice a day; the third LED in each signal device (i.e., the LEDs numbered "3"), corresponds to a frequency of three times a day; the fourth LED in each signal device (i.e., the LEDs numbered "4"), corresponds to a frequency of four times a day; and the fifth LED in each signal device (i.e., the LEDs numbered "5"), corresponds to a frequency of five times a day. If more frequencies are desired (e.g., six times a day, eight times a day, and so on) additional LEDs can be added to each of the signal devices 108, 112 and 116.

As described above, for the exemplary device 100 the "tasks" are "BLOOD PRESSURE" (first task), "ASTHMA" (second task), and "ANTIBIOTICS" (third task). By way of example, let us assume that a user is to take the Blood Pressure medication twice daily, the Asthma medication once a day, and the Antibiotics four times per day. The user (or care-giver) applies the identifications of these three "tasks" to the surface 124. Then, to set the reminders, the user proceeds as follows. For the first reminder (for "BLOOD PRESSURE"), the user presses and holds the first task switch 102. While the task switch 102 is held, the first LED 110 (the LED numbered "1"), will briefly illuminate. After a short period of time (for example, one second) the second LED (the LED numbered "2") will illuminate. Since this LED corresponds to "twice a day", the dosage frequency of the Blood Pressure medication, the user will then release the task switch, thus causing the first task reminder (for "BLOOD PRESSURE") to be set to alert the user twice a day, beginning 12 hours from the time that the reminder has been set (i.e., "programmed").

Likewise, for the second reminder (for "ASTHMA"), the user presses and holds the second task switch 104. While the task switch 104 is held, the first LED 114 (the LED numbered "1"), will briefly illuminate. Since this LED corresponds to "once a day", the dosage frequency of the Asthma medication, the user will then release the task switch, thus causing the second task reminder (for "ASTHMA") to be set to alert the user once a day, beginning 24 hours from the time that the reminder has been set.

Finally, for the third reminder ("ANTIBIOTICS"), the user will press and hold the third task switch 106 until the fourth LED (the LED 118 numbered "4") in the signal device 116 is sequentially lit (in the manner described above for the first task reminder programming). Once the fourth LED is illuminated, the user will release the task switch 106, thus causing the third task reminder (for "ANTIBIOTICS") to be set to alert the user four times a day, beginning 6 hours from the time that the reminder has been programmed.

Subsequently, the third reminder will be initiated after 6 hours, being the first of the three reminders which will be generated by the program entered in the example above (and assuming that all of the reminders are programmed at the same time). The third task reminder is generated by causing one or more of the LEDs in the third signal device 116 to illuminate. Preferably, the fourth LED in the third signal device is the LED that is illuminated, which serves not only to remind the user to take or administer the Antibiotics at this time, but also reminds the user that this medication is to be taken four times a day. When an audible alarm 122 is also provided, the audible alarm can sound at the same time that the signal device 116 provides a visual reminder. As discussed above, the audible reminder can be varied depending on which task is currently being reminded. For example, for the third task, the audible alarm can consist of three short "beeps", followed by a pause (for example, thirty seconds), and then the three "beeps" repeat. The apparatus can be provided to continue to provide the reminder continuously until the user acknowledges the reminder. However, the apparatus can also be configured to cancel the reminder after a predetermined period of time (for example, after one hour).

The user can acknowledge the reminder by pressing the corresponding task switch 102, 104, 106, 134, 136 or 138 a single, short time (rather than pressing and holding the task switch, as is done during the programming (i.e., setting) phase, described above). Acknowledging the reminder causes the signal device (and the audible reminder, when used), to cease generating the reminder.

In the above example, after reminder for the third "task" (Antibiotics) has been generated, then six hours later the reminders for both the third task and the first task will be generated, corresponding to the second of a four-times-a-day frequency, and the first of a twice-a-day frequency. Six hours thereafter, the third reminder will again be generated, and six hours following that the reminders for all three tasks will be generated. (This assumes that the reminders were all programmed at the same time.)

To cancel a reminder program for a particular task, if the apparatus 100 is provided with reset switches 134, 136 and 138, then by pressing a reset switch for an associated task, the reminder program is terminated, and no more reminders will be generated for that task unless the user once again programs or sets the apparatus to generate reminders for that task. The apparatus can also be configured without the reset switches, in which case a reminder program can be canceled by pressing and holding the task switch associated with the task until the signal device indicates that no interval has been set. For example, to cancel the reminder program for the first task, a user presses and holds the first task switch 102. As the switch is held, the LEDs 110 in the first signal device 108 sequentially illuminate. After the last LED 110 (the LED numbered "5") has illuminated and is no longer illuminated, the user releases the task switch, and no reminders are now set for the first task.

In an alternate configuration, the processor can be programmed such that the user presses the task switch for a short interval (e.g., less than two seconds) a number of times until the desired frequency of alarming is set. For example, with reference to FIG. 1, if the user presses the task switch 102 three times in succession, each time pressing the switch 102 for less than two seconds, the third indicator 110 (identified as LED 3) will be illuminated, and thus the apparatus 100 will be set to generate an alarm three times per day. However, if the user holds the task switch 102 for more than two seconds, then the alarm feature for task 1 will be canceled.

Figure 3A:
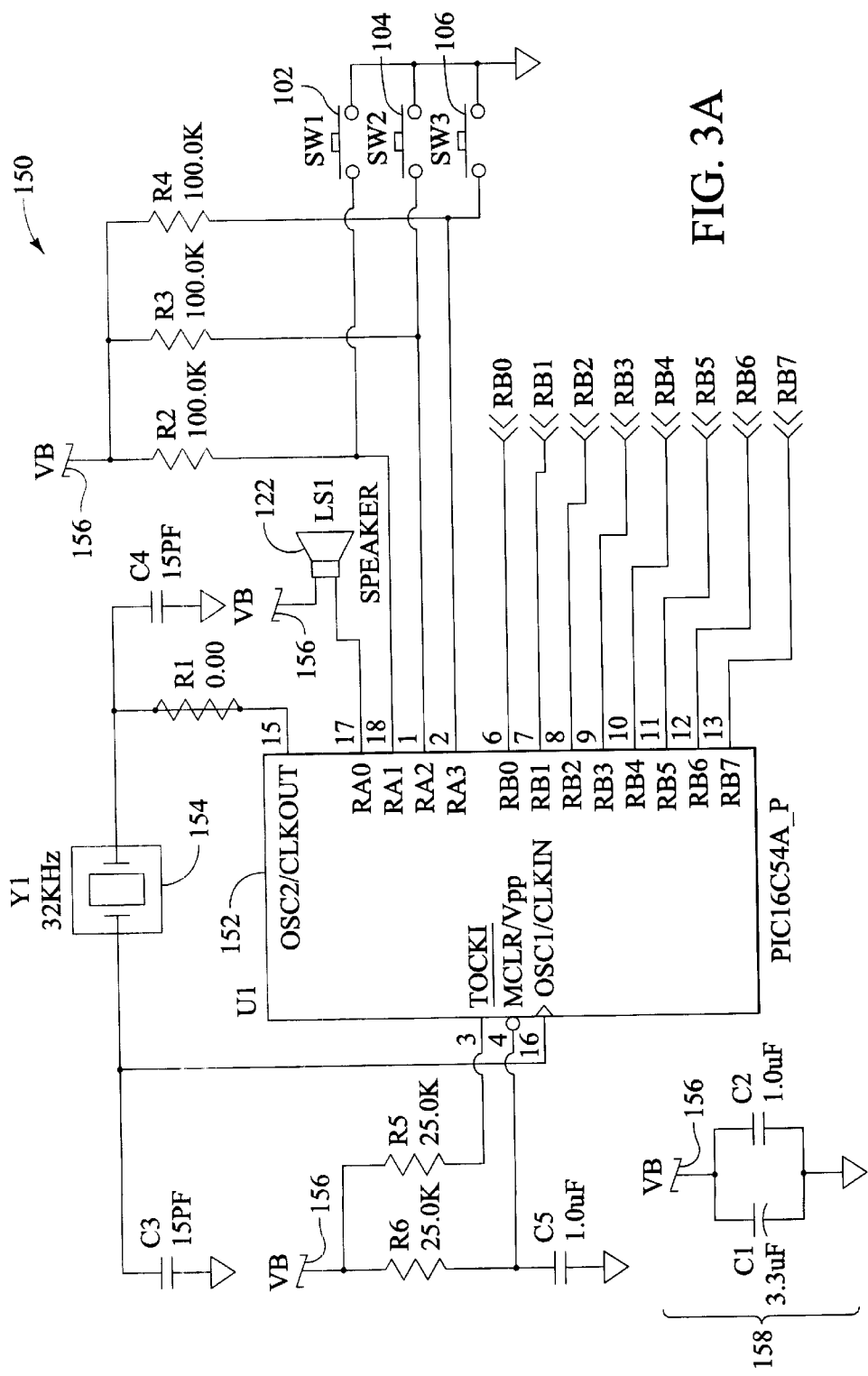
FIGS. 3A and 3B together depict a schematic diagram showing an electronic circuit which can be used to implement the apparatus of FIG. 1.
Figure 3B:
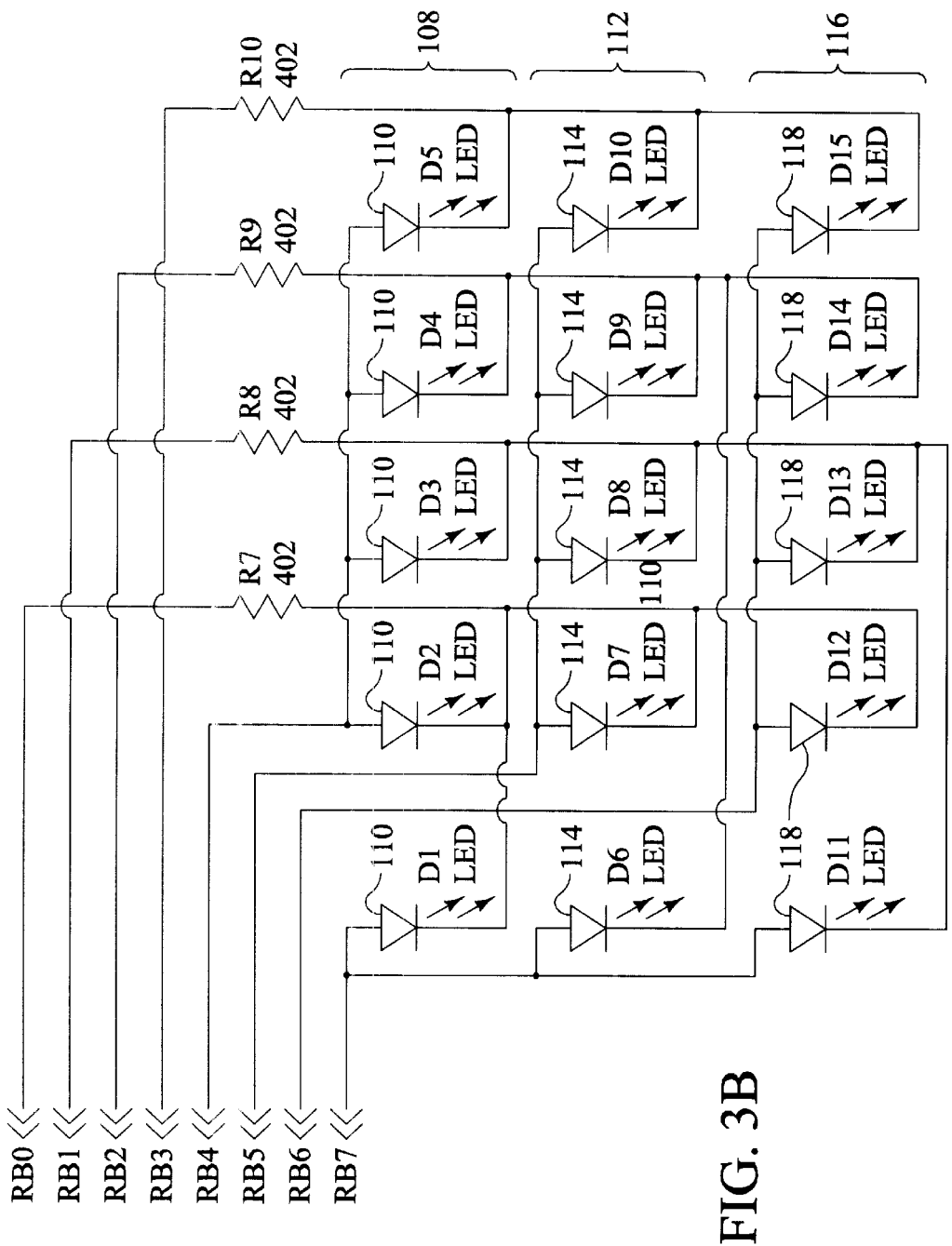

Turning now to FIGS. 3A and 3B, a circuit diagram of an electronic circuit 150 which can be used to implement the apparatus 100 of FIG. 1 is depicted. The circuit 150 includes an electronic processor 152 (FIG. 3A). In the example depicted, the processor is a programmable processor which can execute a series of executable steps (i.e., a "program") to perform the functions described herein. However, it will be appreciated by those skilled in the art that a processor using logic gates and state circuits can also be used to implement an apparatus in accordance with the present invention. The process or does not need to be contained on a single microchip, but can comprises plurality of microchips which in conjunction perform the functions described. The processor is in electronic communication with the signal devices 108, 112 and 116 (FIG. 3B), which comprise the respective LEDs 110, 114 and 118 (also FIG. 3B), which are also depicted in FIG. 1. The processor 152 is further in electronic communication with the task switches 102, 104 and 106 (FIG. 3A), which are those task switches depicted in FIG. 1. The circuit 150 further includes an electronic timing device, which is depicted here as the oscillating crystal 154 (FIG. 3A). The crystal 154 oscillates at a known, consistent rate (here, 32 KHz), and can thus act as a "clock" to time intervals for generating the reminders. The circuit 150 also includes an audible alarm 122 (FIG. 3A), as also depicted in FIG. 1. The circuit 150 can be powered by a battery (not shown), which connects to the points in the circuit diagram identified as "VB" ("voltage-battery"). Filter 158 (FIG. 3A) can be used to isolate the processor 152 from noise generated by the oscillator 154.

The circuit 150 also incorporates an electronic readable-writeable memory device (not shown), which can be resident on the same microchip(s) as contains the processor 152. Accordingly, the depicted device as 152 (FIG. 3A) is both the processor and the electronic readable-writeable memory device. One example of a readable-writeable memory device is a random access memory (RAM) which defines a plurality of memory locations. The memory device can also include portions which are readable and writeable, as well as portions which are readable only, such as read-only-memory ("ROM"). For example the executable steps to be performed by the processor 152 can be stored in the read-only-memory portion of the readable-writeable memory device. Thus, the memory device can comprise a plurality of microchips (RAM and ROM), which together make up the memory device.

The writeable memory locations in the memory device can be written with a first value, and later rewritten with a different value. The memory locations can also be assigned different functions. For example, the memory device can have "task memory locations", which can further be assigned as either "primary task memory locations" or "secondary task memory locations". Preferably, each task is associated with both a preassigned primary memory location and a preassigned secondary memory location. For example, the first task has a first task primary memory location, and a first task secondary memory location; the second task has a second task primary memory location, and a second task secondary memory location; and so on. An interval value, or alarm interval, corresponding to the time between reminders to be generated for a particular task, is stored in the corresponding primary memory location. For example, when a reminder for the first task is to be generated every 12 hours, then a value equivalent to this duration of time is stored in the first task primary memory location. This can be achieved using the first task switch 102 in the manner described above with respect to the operation of the apparatus 100 of FIG. 1.

The secondary task memory locations can be used to store an increasing value, which essentially corresponds to the passage of time since a reminder was initially set or was last generated. This increasing value can be generated by the electronic timing device 154. Each time the timing device cycles, a new, incremental value is stored in the secondary task memory locations. The processor is thus configured to compare each primary task memory location to its corresponding secondary task memory location. When the increasing value in the secondary memory location is equal to or greater than the interval value stored in the corresponding primary memory location, then the processor generates a reminder or alarm for the associated task in the manner described above.

The processor can be further provided with executable steps to generate a distinct audible alarm, or to otherwise vary the reminder signal or alarm signal, depending on which of the tasks the alarm signal is being generated for. As an example, if the reminder is to be generated for the second task, then the processor can vary the audible signal by generating two short "beeps", or it can flash an LED in the signal device associated with the second task. The processor can also be provided with an executable step to cancel a reminder once a task switch is accessed for less than a predefined period of time.

Figure 4:
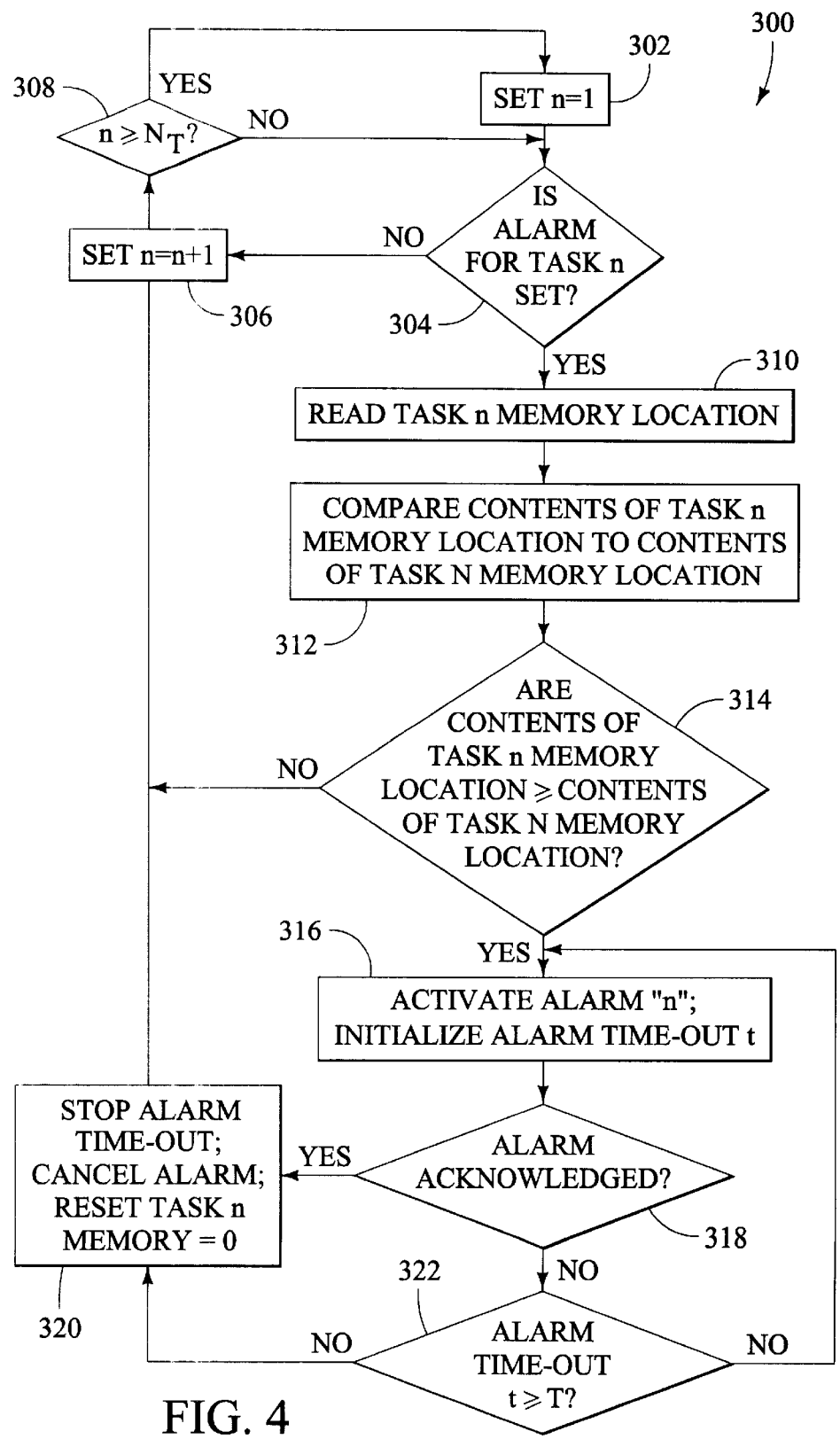
FIG. 4 is a diagram depicting a flowchart of one method for implementing the apparatus of FIGS. 1 and 3A–3B.

Turning to FIG. 4, a flow chart 300 is depicted which illustrates one method of configuring a processor (such as processor 152 of FIG. 3A) to implement an apparatus in accordance with the present invention, and particularly the apparatus 100 of FIG. 1. The flow chart assumes that a reminder regime has been entered into the apparatus, as for example in the manner described above. The flow chart causes the processor to consider whether a reminder should be generated for a given task "n", being one of a total number of tasks "$N_T$". For example, the apparatus 100 of FIG. 1 allows for three reminders to be set for three different tasks, so n=1, 2 and 3, wherein $N_T$ is 3. That is, the task n=1 is a reminder for BLOOD PRESSURE, task n=2 is a reminder for reminder for ASTHMA, and task n=3 is a reminder for ANTIBIOTICS. In general, the processor uses a task counter to look at each task in sequence, and after all of the tasks (i.e., $N_T$ tasks) have been reviewed (and acted on, if necessary), the processor then starts the process over again, beginning with the first task (i.e., n=1).

At step 302 of the flow chart 400 the processor sets a task counter for task "n" equal to "1", being the first task. At step 304 the processor checks to determine whether a reminder (an "alarm") has been set for that task. If not, at step 306 the processor increments the task counter by 1, and then at step 308 checks to determine whether the current value of "n" exceeds the total number of tasks $N_T$. If the total number of tasks has been exceeded by the counter, the processor returns to step 302 and resets the task counter to 1. However, if the task counter has not exceeded the total number of tasks, then from step 308 the processor proceeds to step 304 to determine whether an alarm has been set for that task.

If at step 304 the processor determines that an alarm or reminder has been set for the task indicated by the task counter, then at step 310 the processor reads the contents of a memory location associated with the task, which essentially corresponds to the secondary memory location described above with respect to FIG. 3A. That is, the processor reads the memory location which records the passage of time since the reminder was initiated or last generated. At step 312 the processor compares the value read in step 310 with a value stored in a memory location "N", which corresponds to the primary task memory location described above. That is, the value stored in memory location "N" is the duration of time between reminder intervals for the particular task. If at step 314 the processor determines that the value stored in memory location "n" is less than the value in memory location "N", this indicates that the reminder interval has not yet expired, and no reminder should be generated. Consequently, the processor returns to step 306 to increment the task counter and repeats the processes already described above with respect to this step.

However, if at step 314 the processor determines that the increasing value in memory location "n" is greater than or equal to the value in memory location "N", then the reminder for task "n" is generated, and at step 316 the processor activates the alarm (for example, using the signal device). The processor also initiates an alarm "time out" timer which records time "t". The time-out function can be used to terminate the alarm after a predetermined period of time "T", for example 20 minutes.

At step 318 the processor checks to determine if the user has acknowledged the alarm. If so, at step 320 the processor stops the time-out timer and resets it to zero, and also stops the alarm. The processor then resets the memory location "n" to zero to begin timing to the next alarm interval, and returns to step 306 to check for the next task "n+1".

If at step 318 the user has not acknowledged the alarm, then at step 322 the processor checks to determine whether the time-out interval "T" has been exceeded. If not, the processor returns to step 318 to determine whether the alarm has been acknowledged. If at step 322 the time-out interval has been exceeded, then the processor proceeds to step 320 to terminate the alarm, reset both the memory location "n" and the time-out counter to zero, and returns to step 306 to check for the next task reminder.

In one variation of the above described program the time-out function can be set by the processor to be a function of the interval frequency, in which case different time-out values can be set for the different tasks, depending on the alarm frequency. For example, if the reminder or alarm frequency is set for three times per day (i.e., every eight hours), then the time out period can be fifty percent of the alarm frequency (i.e., four hours). A time out period of fifty percent of the alarm frequency corresponds to generally recognized good practice in the dispensing of medication. That is, if a patient is to take mediation at a predefined interval (for example, every eight hours), then the patient can take the mediation within the first half of the next interval and still maintain the regimen. However, if the patient does not take the mediation by this time, then the patient should "skip" the current interval and resume taking the mediation at the next recommended opportunity. For example, if a patient is to take mediation at 6 a.m. and then again at 2 p.m. (i.e., every eight hours), the patient can take the medication at any time between 6 a.m. and 10 a.m., and then again at 2 p.m., and still stay on the defined regimen. However, if the patient has not taken the prescribed 6 a.m. dosage by 10 a.m., then the patient should "skip" the 6 a.m. dosage and resume the medication dosage regimen at 2 p.m. Providing a time-out duration of fifty percent of the selected interval thus corresponds to this generally recommended practice.

Figure 2:
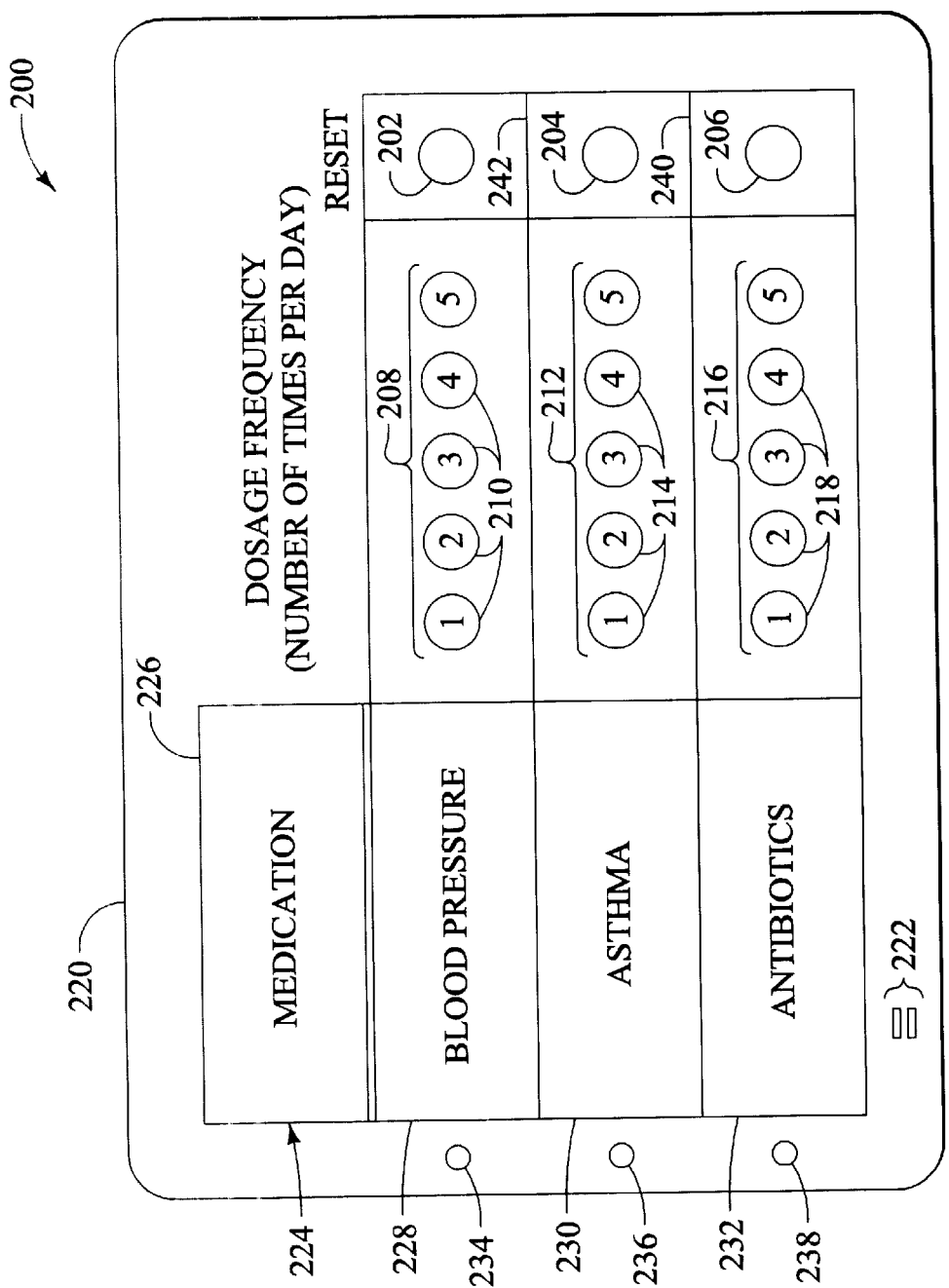
FIG. 2 is a plan view of an apparatus in accordance with a second embodiment of the present invention.

Turning now to FIG. 2, a plan view of an apparatus 200 in accordance with a second embodiment of the present invention is depicted. The apparatus 200 includes a body member 220 similar to the body member 120 of FIG. 1. The apparatus further includes a surface 224, similar to the surface 124 of FIG. 1, upon which can be imprinted tasks 228, 230 and 232, and a task type identifier 226. The apparatus includes signal devices 234, 236 and 238 which are associated with respective tasks 228, 230 and 232. The signal devices can be for example individual light emitting diodes. Each identifiable task also has an associated user-accessible interface 208, 212 and 216. Each user-accessible interface comprises a series of task switches, respectively 210, 214 and 218. Each task switch corresponds to the frequency of a reminder to be generated for the associated identifiable task. For example, the task switch 210 identified as "1" corresponds to a reminder frequency of "one time per day" for the first task 228. Likewise, the task switch 210 identified as "5" corresponds to a reminder frequency of "five times per day" for the first task 228, and the task switch 214 identified as "3" corresponds to a reminder frequency of "three times per day" for the second task 230. The apparatus can also include respective reset switches 202, 204 and 206. An audible alarm 222, similar to the audible alarm 122 of FIG. 1, can also be provided.

The operation of the apparatus 200 of FIG. 2 is slightly different than that of the apparatus 100 of FIG. 1. Since each user interface 208, 212 and 216 comprises a plurality of task switches corresponding to the desired reminder frequency, the user can set (i.e., "program") a reminder frequency for a task merely by pressing the specific task switch which corresponds to the desired reminder frequency. For example, if the user desires to be reminded four time per day for the "task" of "ANTIBIOTICS", then the user merely presses the task switch 218 identified as "4" a single time, and the reminder is set. When a reminder is generated for a particular task, the user can be notified by the signal device associated with the task. The user can acknowledge an alarm by pressing the task switch while the reminder alarm is being generated. To clear a programmed reminder for a task, the user merely presses the reset switch associated with the task. Alternately, the reminder for a task can be cleared by pressing the task switch a second time. (That is, the task switch can be pressed once to set the reminder, and then a second time to clear the reminder.)

Figure 5:
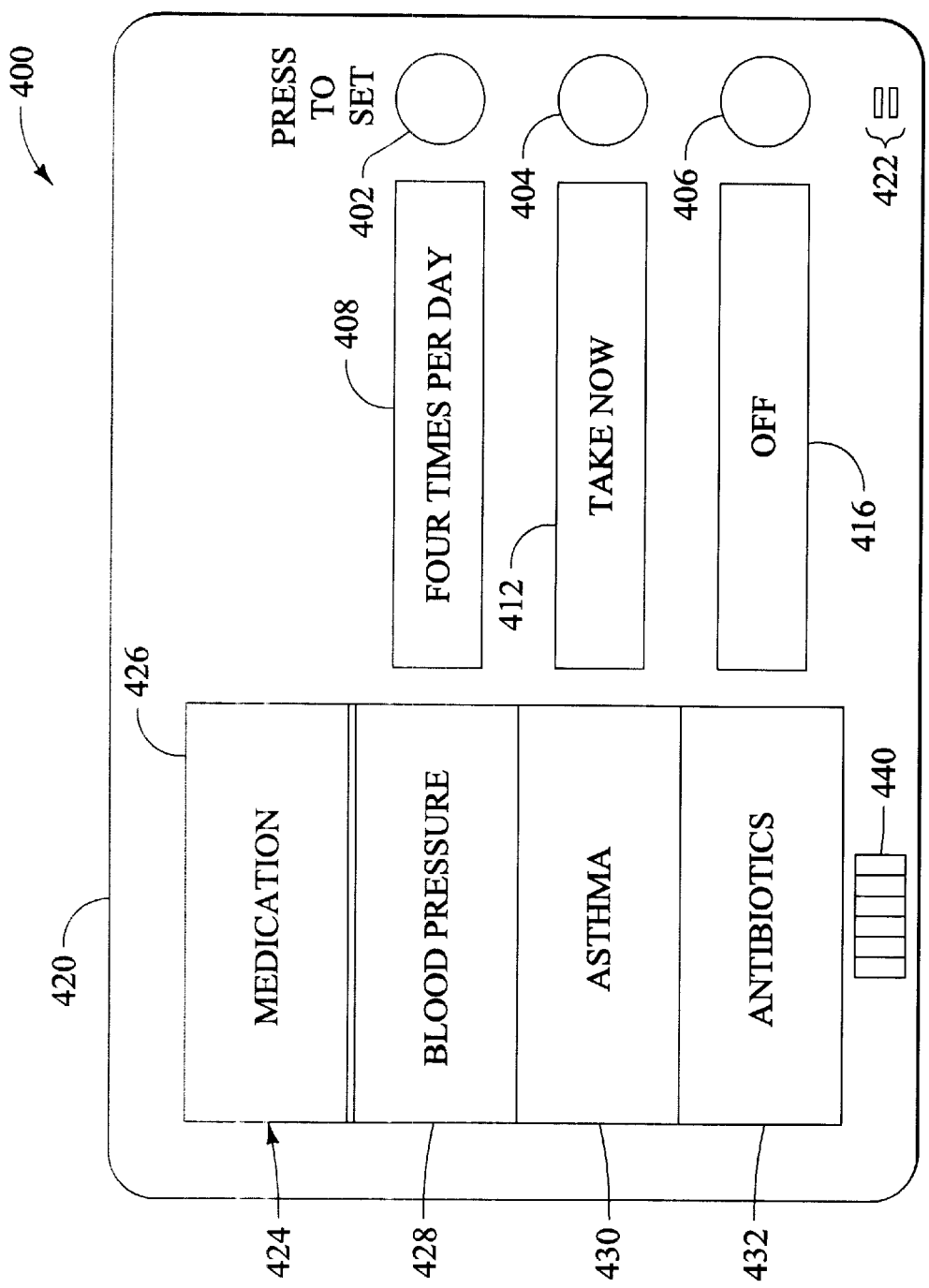
FIG. 5 a plan view of an apparatus in accordance with a third embodiment of the present invention.

Turning to FIG. 5, a plan view of an apparatus 400 in accordance with a third embodiment of the present invention is depicted. The apparatus 400 includes a body member 420 similar to the body member 120 of FIG. 1. The apparatus further includes a surface 424, similar to the surface 124 of FIG. 1, upon which can be imprinted tasks 428, 430 and 432, and a task type identifier 426. In one variation, rather than being powered by a battery, the apparatus 400 (and likewise the apparatus 100) can be powered by a photovoltaic cell, such as cell 440. The apparatus 400 is similar to the apparatus 100 in that it is configured to allow the reminders for the tasks to be programmed using a single task switch and a single keystroke. Accordingly, the apparatus 400 includes task switches 402, 404 and 406 for respective identifiable tasks 428, 430 and 432. However, in the apparatus 400, the signal devices 408, 412 and 416 comprise liquid crystal displays (LCDs) having the capability to either display text, numerical information, symbols, or any combination thereof. The apparatus 400 can further comprise an audible alarm 422.

The programming of the apparatus 400 is similar to that of the apparatus 100 of FIG. 1. That is, a user presses and holds one of the task switches 402, 404 or 406 until the desired function is made available to the user, at which point the user releases the task switch and the function is set. For example, by pressing and holding task switch 402, the signal device, LCD 408, displays a scrolling menu to the user. More specifically, the LCD can display the message, "ONE TIME A DAY" for the first 2 seconds that the task switch 402 is held down, "TWO TIMES A DAY", during the next two seconds, "THREE TIMES A DAY", for the following two seconds, and soon. In this manner a large number of reminder frequencies can be made available to the user without the limitations presented by the configuration of FIG. 1, wherein a dedicated LED is provided for each reminder frequency. As the LDC scrolls through the reminder frequencies provided to the user, the user can select a reminder frequency merely by releasing the task switch. The apparatus is then programmed to generate reminders for the associated task on this schedule. If no reminder frequency is selected by the user, once the last frequency has been offered, the next selection can be "OFF", which effectively disables any reminders for the associated task.

When a reminder is generated by the apparatus 400, a message can appear in the LCD informing the user that the task should be performed. For example, in signal device 412 the message is, "TAKE NOW", reminding the user to take the asthma medication at this time. The user can acknowledge the reminder by pressing the task switch 404 a single time.

Each of the messages which can be displayed by the LCD signal devices can be stored in a read-only-memory device, such as was described above with respect to circuit 150 of FIGS. 3A and 3B. The processor 152 (FIG. 3A) can be configured to display the different messages based on a timed interval during which a task key is enabled. This can be accomplished using the writeable memory and the electronic timer 154. For example, when task switch 402 is accessed, the timer is initiated, and the incrementing time interval is stored in a task switch memory location. When the time interval in the task switch memory location is between zero and two seconds, the processor displays the message, "ONE TIME A DAY". When the time interval in the task switch memory location is between two and three seconds, the processor displays the message, "TWO TIMES A DAY", and so on. When the task switch 402 is released, the timer is halted, and the processor is configured to detect the changed state of the task switch, and in response the processor stores the most recent reminder interval (e.g., "one time a day", "two times a day", and so on) in a primary memory location (e.g., location "N" of step 314, flow chart 300, FIG. 4). The processor then clears the task switch memory location, and proceeds to record the passage of time for the task in the associated secondary task memory location, in the manner described above with respect to the circuit diagram 150 of FIGS. 3A and 3B and the flow chart 200 of FIG. 4.

While the above invention has been described in language more or less specific as to structural and methodical features, it is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An apparatus for reminding a person to perform a plurality of periodically repeating tasks, comprising:
    a body member;
    a first and a second user-accessible task switch supported by the body member;
    a first signal device and a second signal device, each said signal device aligned with the respective first and second task switches, the signal devices supported by the body member;
    a surface supported by the body member and configured to be imprinted with a first and a second task identification, such that when the task identifications are imprinted on the surface the first and second task identifications are aligned with the corresponding first and second signal devices and the first and second task switches;
    an electronic processor in electronic communication with the first and second task switches and the first and second signal devices;
    an electronic timing device;
    an electronic readable-writeable memory device defining a first task primary memory location, a first task secondary memory location, a second task primary memory location, and a second task secondary memory location; and
    wherein the processor is configured to:
        generate a predetermined signal when a user actuates one of the first or second task switches in a predefined manner, thereby causing an interval value to be stored in the corresponding first or second task primary memory location, and further causing the corresponding first or second signal device to indicate to the user via the respective first or second signal device an alarm interval corresponding to the interval value;
        store in the first and second task secondary memory locations an increasing value as determined by the electronic timing device; and
        generate an alarm signal when the increasing value in one of the first or second task secondary memory locations is greater than the interval value in the corresponding first or second task primary memory locations.

2. The apparatus of claim 1, and wherein the alarm signal is used to generate a visible signal using the signal device corresponding to the secondary memory location which caused the alarm signal to be generated.

3. The apparatus of claim 1, and wherein the first and second signal devices each comprise a plurality of light emitting diodes.

4. The apparatus of claim 1, and wherein the first and second signal devices each comprise a liquid crystal display.

5. The apparatus of claim 1, and further comprising an audible alarm, and wherein the audible alarm is configured to be activated by the alarm signal.

6. The apparatus of claim 1, and further wherein the alarm interval corresponds to a periodic frequency occurring at most once every twenty-four hours.

7. The apparatus of claim 1, and wherein the processor is a programmable processor, and further wherein the readable-writeable memory device contains a series of executable steps which can be accessed by the processor and executed by the processor to vary the interval value stored in the memory device in response to the user accessing the first or second task switches.

8. The apparatus of claim 7, and wherein:
    the first and second task switches are configured to be cycled by the user between an open state and a closed state; and
    the readable-writeable memory device further contains executable steps to vary the interval value stored in the first or second task primary memory location when the respective first or second task switch is held in a continuous closed state for longer than a predetermined period of time.

9. The apparatus of claim 7, and wherein the readable-writeable memory device further contains executable steps to vary the alarm signal depending upon whether the alarm signal is generated by the increasing value in the first or the second task secondary memory locations.

10. The apparatus of claim 7, and wherein the readable-writeable memory device further contains executable steps to cancel the alarm signal in response to the user accessing one of the first or the second task switches.

11. The apparatus of claim 7, and wherein the readable-writeable memory device further contains executable steps to cancel the alarm signal after a predetermined period of time.

12. The apparatus of claim 1, and wherein the readable-writeable memory device further contains executable steps to initialize the first or second task secondary memory location to zero when the alarm signal generated by the respective first or second primary memory locations is canceled, and to thereafter again store the increasing value in the respective first or second task secondary memory locations.

13. The apparatus of claim 1, and further wherein the surface supported by the body member is an essentially planar component removable from the body member.

14. The apparatus of claim 1, and further comprising a first and a second reset switch, and in response to the user accessing the first or second reset switch, the processor is prevented from generating the alarm signal corresponding to the first or the second task secondary memory locations.

15. An apparatus for reminding a person to perform a plurality of periodically repeating tasks, comprising:
    a body member;
    a first plurality and a second plurality of user-accessible task switches supported by the body member, each task switch in the plurality of task switches corresponding to a distinct time interval;
    a first signal device and a second of signal device, each said signal device corresponding to the respective first and second task plurality of task switches, the signal devices supported by the body member;
    a surface supported by the body member and configured to be imprinted with a first and a second task identification, such that when the task identifications are imprinted on the surface the first and second task identifications are aligned with the corresponding first and second signal devices and the first and second plurality of task switches;

an electronic processor in electronic communication with the first and second plurality of task switches and the first and second signal devices;

an electronic timing device;

and wherein the processor is configured to:
- set a first alarm interval in response to one of the first plurality of task switches being accessed by a user, and set a second alarm interval in response to one of the second plurality of task switches being accessed by a user;
- measure the passage of time using the electronic timing device;
- activate the first signal device when the measured passage of time exceeds the first alarm interval; and
- activate the second signal device when the measured passage of time exceeds the second alarm interval.

16. The apparatus of claim 15, and further comprising a first reset switch configured to terminate the activation of the first signal device, and a second reset switch configured to terminate the activation of the first signal device.

17. The apparatus of claim 15, and wherein the first and second signal devices are light emitting diodes.

18. The apparatus of claim 15, and further comprising an audible alarm device, and wherein the audible alarm is activated when either of the first or the second signal devices are activated.

19. The apparatus of claim 18, and wherein the audible alarm device emits a first audible signal in response to activation of the first signal device, and a second audible signal in response to activation of the second signal device.

20. An apparatus for reminding a person to perform a plurality of periodically repeating tasks, comprising:
- a body member;
- a first and a second user-accessible interface, each said interface comprising at one least task switch supported by the body member;
- a first signal device and a second signal device, each said signal device aligned with the respective first and second user-accessible interfaces, the signal devices supported by the body member;
- a surface supported by the body member and configured to be imprinted with a first and a second task identification, such that when the task identifications are imprinted on the surface the first and second task identifications are aligned with the corresponding first and second signal devices and the first and second user-accessible interfaces;
- an electronic processor in electronic communication with the first and second user-accessible interfaces and the first and second signal devices;
- an electronic timing device;

and wherein the processor is configured to:
- set a first alarm interval in response to the at least one task switch of the first user-accessible interface being accessed by a user a single time, and set a second alarm interval in response to the at least on a task switch of the second user-accessible interface being accessed by a user a single time;
- measure the passage of time using the electronic timing device;
- activate the first signal device when the measured passage of time exceeds the first alarm interval; and
- activate the second signal device when the measured passage of time exceeds the second alarm interval.

21. An apparatus for reminding a person to perform a plurality of periodically repeating tasks, comprising:
- a first and a second user-accessible interface, each said interface having at least one task switch;
- a first and a second signal device, each said signal device aligned with the respective first and second user-accessible interfaces;
- a surface supported by the apparatus configured to be imprinted with first and second task identifications which are aligned with at least one of the corresponding signal devices or user interfaces;
- an electronic timing device; and
- an electronic processor configured to:
  - set a first alarm interval and a second alarm interval in response to the respective task switches each being accessed by a user a single time;
  - measure the passage of time using the electronic timing device; and
  - activate the first or second signal device when the measured passage of time exceeds the respective first or second alarm interval.

* * * * *